US005731275A

United States Patent [19]
Prevost et al.

[11] Patent Number: 5,731,275
[45] Date of Patent: Mar. 24, 1998

[54] SYNERGISTIC DETERGENT AND DISINFECTANT COMBINATIONS FOR DECONTAMINATING BIOFILM-COATED SURFACES

[75] Inventors: André Prevost; Jean Barbeau, both of Montréal; Ludger Cote, Matane; Robert Charland, Boucherville; Esther Faucher, Montréal, all of Canada

[73] Assignee: Universite de Montreal, Canada

[21] Appl. No.: 367,009

[22] Filed: Dec. 30, 1994

Related U.S. Application Data

[63] Continuation-in-part of Ser. No. 223,157, Apr. 5, 1994, abandoned.

[51] Int. Cl.$^6$ ............................... C11D 9/50; C11D 3/48
[52] U.S. Cl. ................. 510/161; 510/370; 510/383; 510/386; 510/426; 510/434; 510/199
[58] Field of Search .......................... 252/95, 100, 102, 252/104, 106, 142; 510/161, 307, 370, 372, 375, 382, 383, 386, 426, 434, 480, 488, 495, 199

[56] References Cited

U.S. PATENT DOCUMENTS

| | | | |
|---|---|---|---|
| 3,969,498 | 7/1976 | Catania et al. | 424/28 |
| 4,115,293 | 9/1978 | Schoenholz | 252/102 |
| 4,391,287 | 7/1983 | Konoshima | 134/99 |
| 4,448,750 | 5/1984 | Fuesting | 422/20 |
| 4,526,751 | 7/1985 | Gartner | 422/37 |
| 4,545,956 | 10/1985 | Ciszewski et al. | 422/28 |
| 4,738,840 | 4/1988 | Simon et al. | 424/51 |
| 4,770,884 | 9/1988 | Hill | 426/332 |
| 4,839,080 | 6/1989 | Jungermann et al. | 252/107 |
| 4,923,809 | 5/1990 | Otsuji et al. | 435/101 |
| 4,933,179 | 6/1990 | Allison et al. | 424/89 |
| 4,976,969 | 12/1990 | Plamondon | 424/672 |
| 5,008,030 | 4/1991 | Cook et al. | 252/106 |
| 5,038,769 | 8/1991 | Krauser | 128/203.27 |
| 5,049,299 | 9/1991 | Bunczk et al. | 252/106 |
| 5,118,430 | 6/1992 | Rebouillat et al. | 252/86 |
| 5,165,503 | 11/1992 | Hoffman | 184/55.1 |
| 5,227,161 | 7/1993 | Kessler | 424/94.4 |
| 5,234,832 | 8/1993 | Disch et al. | 435/264 |
| 5,280,042 | 1/1994 | Lopes | 514/557 |
| 5,326,492 | 7/1994 | Hodam, Jr. | 252/106 |
| 5,344,811 | 9/1994 | Bunczk et al. | 504/192 |
| 5,370,534 | 12/1994 | Wolf et al. | 433/80 |
| 5,460,833 | 10/1995 | Andrews | 424/606 |

FOREIGN PATENT DOCUMENTS

| | | |
|---|---|---|
| 0 109 279 | 5/1984 | European Pat. Off. . |
| 0 293 040 A1 | 11/1988 | European Pat. Off. . |
| 0 313 527 | 4/1989 | European Pat. Off. . |
| WO 92 13807 | 8/1992 | WIPO . |
| WO 92 20228 | 11/1992 | WIPO . |
| 94/00548 | 1/1994 | WIPO . |
| WO 95 20366 | 8/1995 | WIPO . |

OTHER PUBLICATIONS

Stickler et al "Activity of Antiseptics against *Esherichia coli*..."Eur. J. Clin. Microbiol. Infect. Dis., Nov. 1989, pp. 974–978.

L.R. Jacquelin et al., "Synergie de L'Association d'Enzymes ou de Surfactant et e'Un Desinfectant Phenolique sur un Biofilm Bacterien", *Pathologie Biologie*, 42(5):425–431 (May, 1994) (English Abstract).

C. Whittaker et al., "Evaluation of cleaning strategies for removal of biofilms from reverse–osmosis membranes", *Applied and Environmental Microbiology*, 48 (3):395–403 (Aug. 1984).

J.R. Marchesi et al., "SDS–degrading becteria attach to riverine sediment in response to the surfactant of its primary biodegradation product dodecan–1–ol" *Microbiology*, 140(11):2999–3006 (Nov. 1994).

Amy B. Ronner et al. "Biofilm development and sanitizer inactivation of *Listeria monocytogenes* and *Salmonella typhimurium* on stainless steel and Buna–n rubber", *Journal of Food Protection*, 58(9):750–758 (Sep. 1994).

*Primary Examiner*—Paul Lieberman
*Assistant Examiner*—Mark Kopec
*Attorney, Agent, or Firm*—Merchant, Gould, Smith, Edell, Welter & Schmidt, P.A.

[57] ABSTRACT

Disclosed herein is a synergistic cleaning and disinfecting composition for use in decontaminating biofilm-coated surfaces like fresh water lines providing water supply to dental instruments, these lines being susceptible to contamination by microorganisms and being susceptible to the formation of biofilm coatings on their inner walls, the composition comprising an effective amount of a detergent, an effective amount of a denaturing agent attacking the extracellular matrix formed between microorganisms and between microorganisms and the inner walls of these water lines and an effective amount of a bactericide for destroying the microorganisms.

4 Claims, No Drawings

SYNERGISTIC DETERGENT AND DISINFECTANT COMBINATIONS FOR DECONTAMINATING BIOFILM-COATED SURFACES

This patent application is a Continuation-In-Part application of Ser. No. 08/223,157, filed Apr. 5, 1994 now abandoned.

BACKGROUND OF THE INVENTION

1. Field of the Invention

The present invention relates to novel synergistic detergent and disinfectant combinations and to an improved method for effectively decontaminating biofilm-coated surfaces. Types of surfaces comprise: the inner surface of aqueous liquid-supplying lines, particularly fresh water lines such as those supplying water to dental instruments regularly used by dentists, dental surgeons or dental hygienists, the inner surface of lines of larger diameters and the inner surface of containers having received aqueous liquids for a sufficient length of time to have allowed growth of microorganisms, their deposition and their organization as a biofilm to adhere to the walls of the containers. More particularly, the present invention relates to detergent-disinfectant combinations for dislodging biofilm formed or accumulated on contaminated surfaces for destroying the microorganisms contained therein. The preferred compositions are particularly suitable for water pipes of dental instruments which are of a small diameter, because no scrubbing is needed for maximal efficiency in a convenient time of decontamination.

2. Brief Description of the Prior Art

Dentists, dental surgeons and dental hygienists and their patients are well aware of the importance of meticulously sterilizing and disinfecting dental instruments. Indeed, since dental instruments are used directly in a patient's mouth, when bleeding may sometimes occur as a result of a dental procedure, it is of paramount importance to minimize the presence of microorganisms carried by dental instruments. The microorganisms can of course range from relatively harmless bacteria to dangerous pathogens. Consequently, efforts are deployed to remove microorganisms from dental instruments and from the fresh water lines feeding dental instruments such as air/water guns, high speed water turbines or ultrasonic tartar removers. For most hand held dental instruments, thermal sterilization remains one of the best methods for eradicating the presence of microorganisms. However, thermal sterilization is obviously not practical for the decontaminating of fresh water lines which remain to this date difficult to rid of microorganisms.

It is well known in the dental profession that small diameter pipes carrying fresh water are contaminated by bacteria and other microorganisms contained in the water flowing through them. Some of the microorganisms inevitably adhere to the inner walls of the pipes and accumulate together with microscopic sediments or other substances into what is commonly known as a biofilm. The biofilm quickly and tenaciously coats the inner walls of the pipes. The biofilm becomes a culture medium for more microorganisms. For example bacteria population will rapidly reach alarming levels which will also be found in the water discharge from the dental instruments connected to the fresh water line. For example, the average bacteria count in the water discharge of dental instruments is known to be of approximately 200,000 colony forming units per milliliter (cfu/ml) and in some extreme cases can reach 10,000,000 cfu/ml.

It has been suggested to use sterile water, to drain the fresh water lines during periods of non-use or to use filters to catch the microorganisms. However, none of those methods have been shown to effectively remedy the microorganism proliferation for any length of time.

It is also known in the art to use disinfectants such as povidone-iodine at a concentration of approximately 10% to reduce the number of microorganisms in small diameter water lines. It is further also known that a mixture of mandelic and lactic acids reduce the number of sensitive microorganisms in contaminated catheters. However, such disinfection is somewhat superficial since it fails to effectively attack and destroy the microorganisms found in the biofilm. Consequently, the disinfection effect is short-lived. After 24 hours of treatment with povidone-iodine, the number of bacteria is greatly reduced but quickly begin to rise after eight days.

It is also known to use a detergent such as polyoxyethylene sorbitan monooleate (Tween 80™) at approximately 4% concentration to dislodge biofilm from small diameter water lines used in dental equipment. However, the use of detergent alone does not effectively destroy the microorganism population.

Accordingly there remains a need for a composition for decontaminating small diameter water lines for dental equipment which will effectively dislodge and eliminate a biofilm and at the same time destroy the microorganism flora in the fresh water and in the dislodged biofilm.

SUMMARY OF THE INVENTION

The invention provides a synergistic cleaning and disinfecting composition for use in decontaminating biofilm-coated surfaces like the fresh water lines providing water supply to dental instruments, these lines being susceptible to contamination by microorganisms and being susceptible to the formation of biofilm coatings on their inner walls, the composition comprising an effective amount of a detergent and of a denaturing agent affecting the integrity of the proteins and of mucopolysaccharides composing the biofilm for dislodging biofilm accumulation on the inner walls of the lines and an effective amount of a bactericide for destroying the microorganisms within the weakened biofilm or retrieved in suspension.

In the preferred embodiment, the detergent is sodium dodecyl sulfate (SDS) at a 2% concentration. This detergent is the prototype of a class of detergents having denaturant as well as detergent action, so that the addition of a denaturing agent is not necessary and the bactericide is either an acid like lactic and mandelic acids or a potent oxydant like hydrogen peroxyde ($H_2O_2$) and hydrogen peroxyde-stabilized peracetic acid (PAA), the oxydant being combined with a chelating agent like ethylenediaminetetraacetate (EDTA), or a mixture of both an acid and an oxydant/chelating agent.

It should be understood that the detergent component entering the compositions of the present invention is not limited to SDS or SDS-like detergents. Any detergent able to decrease the surface tension of a biofilm and having a denaturant action or combined with a compound having a denaturant action on components of the biofilm e.g. proteins and mucopolysaccharides, notwithstanding the classification of the detergent as a cationic, anionic or nonionic detergent, is under the scope of this invention.

The invention also provides an improved method for cleaning and disinfecting biofilm-coated surfaces like the fresh water lines providing water supply to dental instruments, the water lines being susceptible to contamination by microorganisms and being susceptible to the formation of biofilm coatings on their inner walls, the steps of:

a) draining the water lines;

b) filling the water lines with the decontaminating solution defined in this invention for destroying the microorganisms retrieved in the weakened biofilm or in suspension;

c) leaving the solution in the water lines at ambient temperature for a period of six hours or more;

d) draining the water lines; and e) rinsing the water lines.

Of course, if it impossible or non-convenient to drain the water lines, a part of the liquid may be drained and a suitably concentrated composition may be added to bring the proportions of the active ingredients in final appropriate concentrations. Moreover, if flat surfaces are to be decontaminated, the draining step may be omitted and the composition be spread on the surfaces, in conditions such that the composition will retain its decontaminating activity (for example, by avoiding dehydration). Other features and advantages of the invention will become apparent to those of ordinary skill in the art upon review of the following detailed description and claims.

DETAILED DESCRIPTION OF THE PREFERRED EMBODIMENTS

Surprisingly, the inventors have found synergistic compositions for decontaminating microorganism-contaminated water lines having a biofilm coating the inner walls thereof which comprises the following combinations of ingredients:

1) A suitable detergent for reducing the surface tension of the biofilm;

2) A denaturing agent for affecting the integrity of the proteins and of the mucopolysaccharides, which are bacterial cell components or constituents of the extracellular matrix (the detergent and denaturing functions are both assigned to a detergent like SDS which has being successfully tried at a 2% concentration in distilled water); and 3) A suitable bactericidal component composed of one or more bactericides having a wide spectrum. Bactericides like lactic and/or mandelic acids or of a class of potent oxydants like hydrogen peroxyde ($H_2O_2$) and/or hydrogen peroxyde-stabilized peracetic acid (PAA) or a mixture of both an oxydant and an acid have been successfully tried. In the case wherein an oxydant is used, the combination denaturing detergent/oxydant needs complementation with a chelating agent like ethylenediaminetetraacetate (EDTA).

Those skilled in the art will readily understand and easily conceive other equivalent synergistic compositions containing effective amounts of other suitable denaturants/detergents or other suitable bactericides dissolved in a suitable carrier.

In a preferred embodiment, it has been found that the combination of a denaturing detergent like sodium dodecyl sulfate (SDS) and of a bactericide like either an acid like lactic and/or mandelic acids or a potent oxydant like hydrogen peroxyde ($H_2O_2$) and/or hydrogen peroxyde-stabilized peracetic acid (PAA) (the oxydant being further complemented with a chelating agent like ethylenediaminetetraacetate (EDTA)) has been found advantageous.

A mixture of seven products has been found the most advantageous since its contains:

mandelic acid 1%,
lactic acid 1%,
peracetic acid 1%,
hydrogen peroxyde 5%,
SDS 2%,
EDTA 1%, and
cetylpyridinium chloride 0.1%.

Even though all these combined elements are very efficient in decontaminating fresh water lines, some subcombinations are equally performant. For instance, combinations of SDS and acids like mandelic and lactic acids, having a pK of 3.36 and 3.79, respectively, destroy a biofilm as efficiently as the above complex formulation. A combination like hydrogen peroxyde, SDS and EDTA is also as performant. Another oxydant like peracetic acid is also effective when combined with SDS and EDTA, provided that peracetic acid is stabilized by the presence of hydrogen peroxyde. Therefore, it will be appreciated that many combinations will perform as well as the above combinations and subcombinations. The combination of the seven compounds listed above is particularly advantageous because it contains bactericides which together attack a wide spectrum of sensitive bacteria. Should a resistant bacterium be discovered in the biofilm, this combination of compounds may be amended to include another effective bactericide or it may be complemented by the adjunction of such another bactericide.

Suitable decontaminant solutions should contain a detergent able to decrease the surface tension of the biofilm, a denaturing ingredient capable of decreasing the cohesive force existing between microorganisms and between the microorganisms and the surfaces and a bactericide. A compound like SDS has a dual action as a detergent and as a denaturing ingredient decreasing the cohesive force of components of the biofilm. SDS is indeed a denaturing detergent which attacks the integrity of proteins and of mucopolysaccharides. Compounds like hydrogen peroxyde and hydrogen peroxyde-stabilized peracetic acid also have a dual action as bactericides and potent oxydants which attack the extracellular matrix. Even though lactic acid is not classified as a bactericide, it shown good antibacterial efficiency. Therefore acids like mandelic and lactic acids may have the capacity of killing bacteria sensitive to each or both bactericides after their release from the biofilm or after the weakening of the integrity or of the compacity of the biofilm. A compound like Betadine™ which has a low pH in solution (about 2) may also have such a role (see the Tween 20™/Betadine™ composition in Table 1). By itself, the combination Tween 20™/Betadine™ is not sufficiently effective. It is however believed that this combination would be efficient if supplemented with a denaturing agent and with other bactericides conferring to the combination a more aggressive dislodging power and a larger bactericidal spectrum. When the SDS detergent is used in combination with a potent oxydant like peracetic acid and/or hydrogen peroxyde, these particular combinations need to be complemented by a chelating agent for maximizing the desintegration of the extracellular matrix. This suggests that the denaturing action of SDS is not sufficient by itself to make the biofilm in a state of sufficient vulnerability for the action of this particular type of bactericides; the chelating agent is necessary in this case. This contrasts with the action of mandelic and lactic acids which do not need the complementation by a chelating agent to be effective in combination with SDS. The mechanism of action of these acids on the biofilm is not elucidated. Their efficient action when combined with SDS may suggest that they more accurately affect the integrity of the extracellular matrix and/or that they affect the integrity of the bacteria, in such a way that they facilitate the action of SDS.

In all cases, the synergistic effect of the effective compositions of the present invention can perhaps be explained as follows. It is known that microorganisms present in a biofilm are generally much more resistant to bactericides than microorganisms present in a aqueous medium. The biofilm is thought to act as a physical barrier through which disinfectant agents fail to penetrate and kill the microorganisms present therein. Consequently, in order to eradicate a maximal number of the microorganisms present in small diameter water lines and particularly in the biofilm coating the inner wall of the small diameter water lines, it is important to simultaneously dislodge the biofilm from the inner walls of the lines so that the bactericide can efficiently attack as many microorganisms as possible. In sequence, the denaturing detergent is thought to help the penetration of the bactericide (and the chelating agent when present), dislodge a layer of biofilm which becomes suspended in the small diameter water lines where the bactericide can attack the microorganisms present. This process will expose a lower layer of the biofilm and of living microorganisms which will again be dislodged and killed. The dislodging action of the detergent and of the denaturing agent and the antibacterial action of the bactericide are thus improved.

Combinations containing EDTA may precipitate in the presence of acids. Fortunately, compositions containing SDS and mandelic and lactic acids do not need to be supplemented with EDTA. On the other hand, whenever necessary, it might be possible to choose a salt of a chelator which stays in solution at the desired pH. Also, compositions containing anionic detergents like SDS and a quaternary ammonium precipitate, as this is the case for the combination SDS/cetylpyridinium chloride (CPC). A composition containing a nonionic or a cationic detergent and cetylpyridinium chloride (CPC) has not been tried but it is believed that such a composition may be more suitable than the composition SDS/CPC. Of course, the same principles of efficiency of decontamination apply; such a combination may need to be supplemented with a denaturing agent and/or any ingredient affecting the integrity of the extracellular matrix for maximal efficiency. Also, this combination may be complemented with other bactericides to enlarge its host spectrum.

The formulation of seven ingredients stays in solution even if it contains EDTA and CPC. The presence of a weak acid like peracetic acid appears to help in stabilizing this composition.

When the detergent used in the composition produces foam, it might be desirable to add an anti-foamer. Also, a colorant might be added to the compositions of this invention for easy monitoring of the extent of rinsing.

Fresh water lines supplying dental instruments are of a very small diameter, which excludes the possibility of scrubbing. The compositions of the present invention have the advantage of showing efficient decontamination in the complete absence of scrubbing in a convenient time of decontamination. The present invention is not only useful for dental instruments. It will become obvious that it is intended for other applications, e.g. decontaminating any types of tubing or containers on the surface of which microorganisms are adsorbed and form a biofilm. In such other applications, scrubbing or any other mechanical aid is not at all excluded. Should these compositions be used in pipes of a larger diameter and length, for example, wherein a non-cost effective large volume of decontaminating solution would be needed to fill completely these pipes, it is possible that a mechanical action would help in the distribution of the solution. A mechanical aid, when envisaged, can also help in reducing the duration of decontamination. It is further not excluded to add a vehicle allowing the desinfecting solution to stay in contact with the surface to be decontaminated.

It should also be appreciated that more concentrated solutions could be made inasmuch as the components thereof stay in a solubilized state, otherwise some or all of these components might be delivered in separate vials to be admixed in the final reconstituted volume and proportions of the above effective decontaminating solutions. This could reduce the manutention and storage of large volumes of decontaminating solutions when they are used for desinfecting large surfaces.

EXPERIMENTAL

The synergistic effect of the compositions of the present invention was demonstrated by the following experiment. Four sections of a small diameter (5 mm) water line, contaminated with a relatively thick biofilm on their inner walls were cut and placed in 5 mL test tubes in different decontaminating solutions.

The test tubes were then left for 18–24 hours at 21° C. Each section was then washed with distilled water and slit longitudinally to expose the biofilm on their inner walls and observed with a binocular microscope or by scanning electromicroscopy. Alternatively, the same procedure was followed on plastic plates coated with bacteria. The solutions that showed a significant eradication of the biofilm are listed in Table 1.

TABLE 1

| Substance* | Biofilm presence** | Remarks*** |
|---|---|---|
| Control | ++++ | |
| $H_2O_2$ | ++ | |
| PAA | ++ | |
| SDS | +++ | |
| EDTA | +++ | |
| MA | + | |
| LA | + | |
| CPC | ++ | |
| GLU | + | |
| Solution | 0 | |
| Solution without PAA | 0 | PPT |
| Tween 20 ™ + Betadine | ++ | |
| $H_2O_2$ + PAA | +++ | |
| $H_2O_2$ + SDS | + | |
| $H_2O_2$ + EDTA | ++ | |
| $H_2O_2$ + MA | +− | |
| $H_2O_2$ + LA | + | |
| $H_2O_2$ + CPC | ++ | |
| $H_2O_2$ + PAA + LA | ++ | |
| $H_2O_2$ + PAA + SDS | +− | |
| $H_2O_2$ + MA + LA | +− | |
| $H_2O_2$ + MA + LA + SDS | 0 | |
| $H_2O_2$ + SDS + EDTA | 0 | |
| $H_2O_2$ + PAA + MA | + | |
| SDS + EDTA | +− | |
| SDS + EDTA + MA | 0 | PPT |
| SDS + EDTA + CPC | 0 | PPT |
| SDS + EDTA + PAA | +− | |
| MA + LA | +− | |
| MA + LA + SDS | 0 | |
| MA + LA + EDTA | +− | PPT |
| MA + LA + SDS + EDTA | 0 | PPT |

*MA = Mandelic acid,
LA = Lactic acid,
GLU = Glutaraldehyde,
Peracetic acid = PAA,
Solution = containing all elements listed supra,
Control = Tube without treatment,
SDS = Sodium dodecyl sulfate,
CPC = Cetylpyridinium chloride.
**Solutions were tested directly on contaminated tubes. Results are expressed on a scale representing presence of a biofilm;
0 = no biofilm,
++++ = intact biofilm.
***The solution precipitates.

A field test was conducted over a period of two weeks to four months to determine the cleaning and disinfecting efficacy of the compositions of the present invention. The composition was fed to the network of small diameter fresh water lines of a dentist's installation.

For comparative purposes, at the end of each work day, all the small diameter water pipes of the dentist's installation were filled with the diverse detergent-disinfectant combinations of the present invention, left overnight and the next morning thoroughly rinsed with water.

For each test, during the same work day, three water samples were drawn from various dental instruments, namely, an air/water gun, a high speed water turbine, and an ultrasonic tartar remover. These samples were placed under favourable conditions for microorganism growth. After five to seven days, the microorganism colonies were counted. The results were surprisingly encouraging; after numerous tests on the various instruments, an almost complete abolition of the microbian counts was obtained for the effective combinations of Table 1, e.g. where the presence of biofilm is registered=0. The following antiseptics commercially available have been experimented and none of them have shown any efficient decontaminating activity against a biofilm:

BIOVAC™ (0.8%) Chlorohexidine, 3.20% EDTA, proteolytic enzymes, a dispersing agent).

EFFERDENT™ (Potassium monopersulfate, Sodium borate, Sodium lauryl persulfate, Sodium bicarbonate, Magnesium stearate, Simethicone).

POLYDENT™ (Potassium monopersulfate, Tetrasodium pyrophosphate, Sodium bicarbonate, Sodium borate).

STERISOL™ (Chlorohexidine, Glycerol, 38-F, Alcohol).

THERASOL™ (C-31G, NaF, Glycerine, Alcohol).

GLUTARALDEHYDE

ALCOHOL 70%

PATHEX™ (Phenolic)

SODIUM HYPOCHLORITE 2%.

Apparently, none of these preparations fulfill essential criteria for decontaminating surfaces coated with a biofilm, e.g. a detergent component, a denaturing and matrix-desintegrating component and a bactericide.

Although the present invention has been described hereinabove by way of preferred embodiments thereof, these embodiments can be modified at will, within the scope of the appended claims, without departing from the spirit and nature of the subject invention.

We claim:

1. An aqueous cleaning and disinfecting composition for use in decontaminating surfaces being susceptible to contamination by microorganisms and being susceptible to the formation of a biofilm coating thereon, said composition comprising 2% (w/v) of a mixture of about 1% (w/v) mandelic acid and about 1% (w/v) lactic acid, and 2% (w/v) of sodium dodecylsulfate (SDS).

2. An aqueous cleaning and disinfecting composition for use in decontaminating surfaces being susceptible to contamination by microorganisms and being susceptible to the formation of a biofilm coating thereon, said composition comprising 5% (w/v) hydrogen peroxide, 1% (w/v) ethylenediamine tetraacetic acid (EDTA), 2% (w/v) sodium dodecyl sulfate (SDS), and 2% (w/v) of a mixture of about 1% (w/v) mandelic acid and about 1% (w/v) lactic acid.

3. An aqueous cleaning and disinfecting composition according to claim 2, further comprising 1% (w/v) peracetic acid.

4. An aqueous cleaning and disinfecting composition according to claim 2, further comprising 0.1% (w/v) cetylpyridinium chloride.

* * * * *

UNITED STATES PATENT AND TRADEMARK OFFICE
CERTIFICATE OF CORRECTION

PATENT NO. : 5,731,275
DATED : MARCH 24, 1998
INVENTOR(S) : PREVOST ET AL.

It is certified that error appears in the above-identified patent and that said Letters Patent is hereby corrected as shown below:

Col. 6, line 24: after the words "Table 1" insert —The concentration of the components used to generate data for the substances listed in Table 1 included:

| | |
|---|---|
| mandelic acid | 1% w/v |
| lactic acid | 1% w/v |
| sodium dodecyl sulfate (SDS) | 2% w/v |
| ethylenediamine tetraacetic acid (EDTA) | 1% w/v |
| peracetic acid | 1% w/v |
| hydrogen peroxide | 5% w/v |
| cetylpyridinium chloride | 0.1% w/v— |

Col. 8, line 19, claim 1: "dodecylsulfate" should read —dodecyl sulfate—
Col. 8, line 32, claim 4: "2" should read —3—

Signed and Sealed this

Twenty-sixth Day of September, 2000

*Attest:*

Q. TODD DICKINSON

*Attesting Officer*     *Director of Patents and Trademarks*